United States Patent
Murokh

(10) Patent No.: US 8,430,995 B2
(45) Date of Patent: Apr. 30, 2013

(54) DIELECTRIC PLASMA CHAMBER APPARATUS AND METHOD WITH EXTERIOR ELECTRODES

(75) Inventor: Igor Murokh, Santa Monica, CA (US)

(73) Assignee: Tri-Star Technologies, El Segundo, CA (US)

( * ) Notice: Subject to any disclaimer, the term of this patent is extended or adjusted under 35 U.S.C. 154(b) by 0 days.

(21) Appl. No.: 13/308,495

(22) Filed: Nov. 30, 2011

(65) Prior Publication Data
US 2012/0145673 A1    Jun. 14, 2012

Related U.S. Application Data

(63) Continuation of application No. 11/668,349, filed on Jan. 29, 2007, now abandoned.

(51) Int. Cl.
*H05H 1/24* (2006.01)

(52) U.S. Cl.
USPC .......................................................... 204/164

(58) Field of Classification Search .................. 204/164
See application file for complete search history.

(56) References Cited

U.S. PATENT DOCUMENTS

| | | | |
|---|---|---|---|
| 3,655,438 A | 4/1972 | Sterling et al. | |
| 4,216,254 A | 8/1980 | Lundell et al. | |
| 4,590,842 A | 5/1986 | Goldstein et al. | |
| 5,190,703 A | 3/1993 | Rose et al. | |
| 5,194,291 A | 3/1993 | D'Aoust et al. | |
| 5,316,739 A * | 5/1994 | Yoshikawa et al. | 422/186.05 |
| 5,573,732 A | 11/1996 | Waggener et al. | |
| 5,597,456 A | 1/1997 | Maruyama et al. | |
| 5,776,553 A | 7/1998 | Jaffe et al. | |
| 5,798,146 A | 8/1998 | Murokh et al. | |
| 5,972,176 A | 10/1999 | Kirk et al. | |
| 6,015,759 A | 1/2000 | Khan et al. | |
| 6,053,171 A | 4/2000 | Stewart et al. | |

(Continued)

FOREIGN PATENT DOCUMENTS

| | | |
|---|---|---|
| EP | 1 403 902 A1 | 3/2004 |
| EP | 1403902 | 3/2004 |

OTHER PUBLICATIONS

Kogelschatz, Ulrich Dielectric-barrier Discharges . . . , Plasma Chemistry and Plasma Processing, vol. 23, No. 1, Mar. 2003.

(Continued)

*Primary Examiner* — Kishor Mayekar
(74) *Attorney, Agent, or Firm* — Bruce A. Jagger, Esq.; Wolf, Rifkin, Shapiro, Schulman and Rabkin, LLP

(57) ABSTRACT

A dielectric barrier discharge plasma generator includes a dielectric chamber. The chamber contains or incorporates a solid surface that is to be treated with non-thermal plasma. The chamber can be substantially sealed and confine an atmosphere therein. An atmosphere control system is provided for controlling the atmosphere within the chamber. At least one or two electrodes are located outside of the chamber. When actuated by an appropriate source of plasma generating electrical power the electrodes cause the generation of a solid surface modifying non-thermal plasma in a plasma zone within the chamber. A transport system is provided for moving the electrode and the chamber relative to one another. A plasma zone is confined within the chamber adjacent to the electrodes, and remains substantially stationary relative to the electrodes. The chamber carries the solid surface through the plasma zone. The solid surface remains substantially stationary relative to the chamber.

15 Claims, 5 Drawing Sheets

U.S. PATENT DOCUMENTS

| | | | |
|---|---|---|---|
| 6,082,294 | A | 7/2000 | Simpson |
| 6,156,114 | A | 12/2000 | Bell et al. |
| 6,245,299 | B1 | 6/2001 | Shiloh et al. |
| 6,284,105 | B1 | 9/2001 | Eliasson et al. |
| 6,342,187 | B1 | 1/2002 | Jacob et al. |
| 6,429,889 | B1 | 8/2002 | Murokh |
| 6,455,014 | B1 | 9/2002 | Hammerstrom et al. |
| 6,603,121 | B2 | 8/2003 | Grace et al. |
| 6,632,470 | B2 | 10/2003 | Morra et al. |
| 6,638,484 | B2 | 10/2003 | Nelson et al. |
| 6,664,737 | B1 | 12/2003 | Berry et al. |
| 6,685,803 | B2 | 2/2004 | Lazarovich et al. |
| 6,764,648 | B1 | 7/2004 | Roach et al. |
| 6,776,340 | B2 | 8/2004 | Murokh et al. |
| 6,793,759 | B2 | 9/2004 | Chaudhury et al. |
| 6,896,854 | B2 | 5/2005 | Kong et al. |
| 7,017,594 | B2 | 3/2006 | Kurunczi |
| 2003/0040807 | A1 | 2/2003 | Komvopoulos et al. |
| 2006/0147648 | A1 | 7/2006 | De Vries et al. |

OTHER PUBLICATIONS

Schutze, Andreas . . . , The Atmospheric-Pressure Plasma Jet . . . , IEEE Transactions on Plasma Science, vol. 26, No. 6, Dec. 1998.

Kogelschatz, Ulrich Filamentary, Patterned, and Diffuse Barrier Discharges, IEEE Transactions on Plasma Science vol. 30, No. 4 Aug. 2002.

Nersisyan, G . . . , Characterization of a dielectric barrier . . . Plasma Sources Science and Technology, Sep. 2004, vol. 13, 2004, IOP Publishing Ltd. UK.

Mangolini, L . . . , Radial structure of a low frequency . . . Applied Physics Letters, vol. 80, No. 10, American INstitute of Physics, 2002.

Aldea, E., Generation of a stable atmospheric . . . , Eindhoven University of Technology, The Netherlands.

Larner, Mikki, The challenge of Plasma Processing . . . , ASM Materials and Processes for Medical Devices Conference, Aug. 25-27, St. Paul Minnesota, 2004.

\* cited by examiner

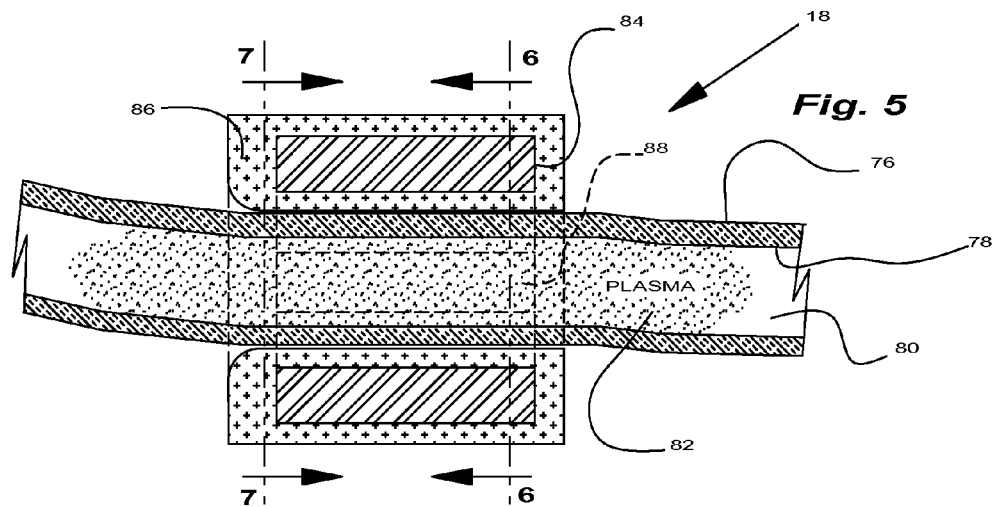
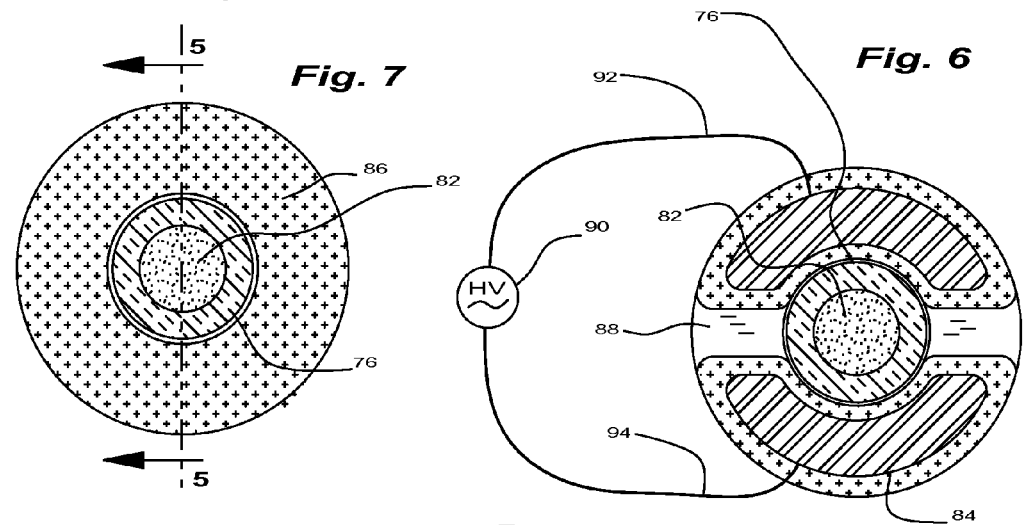
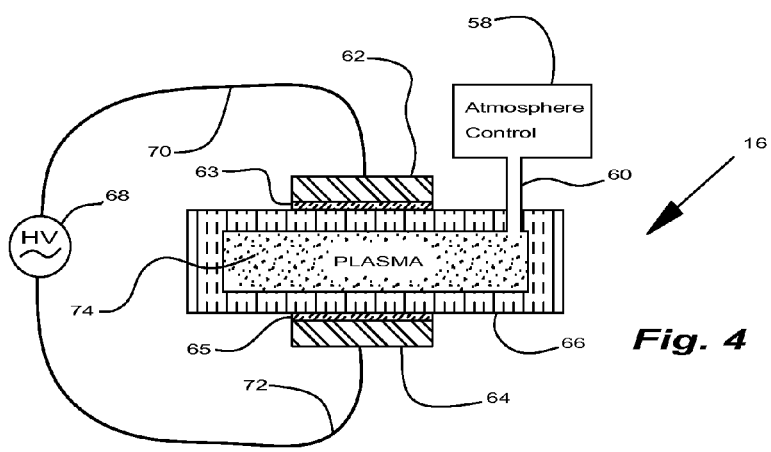

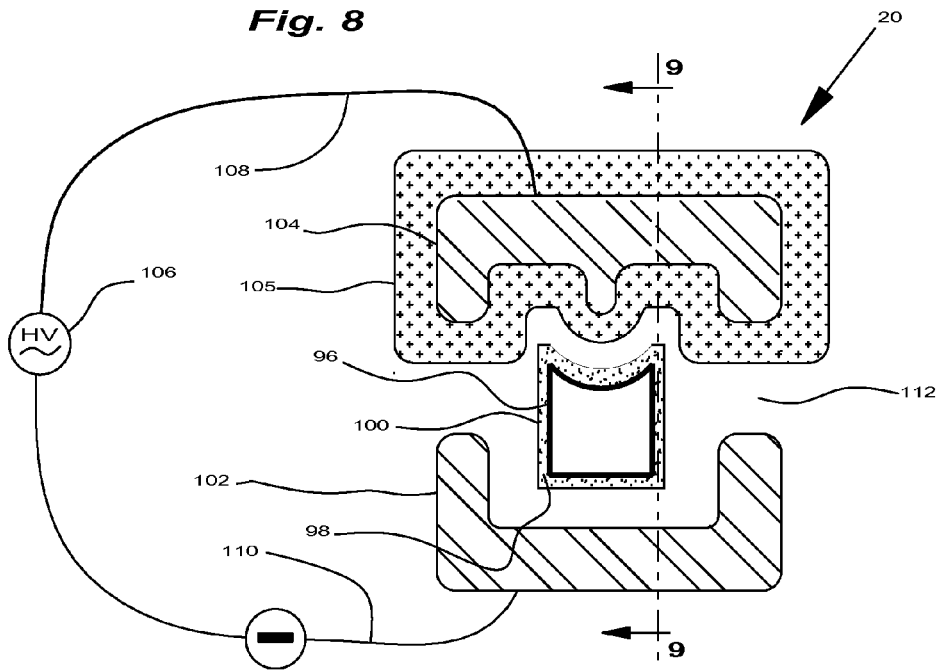
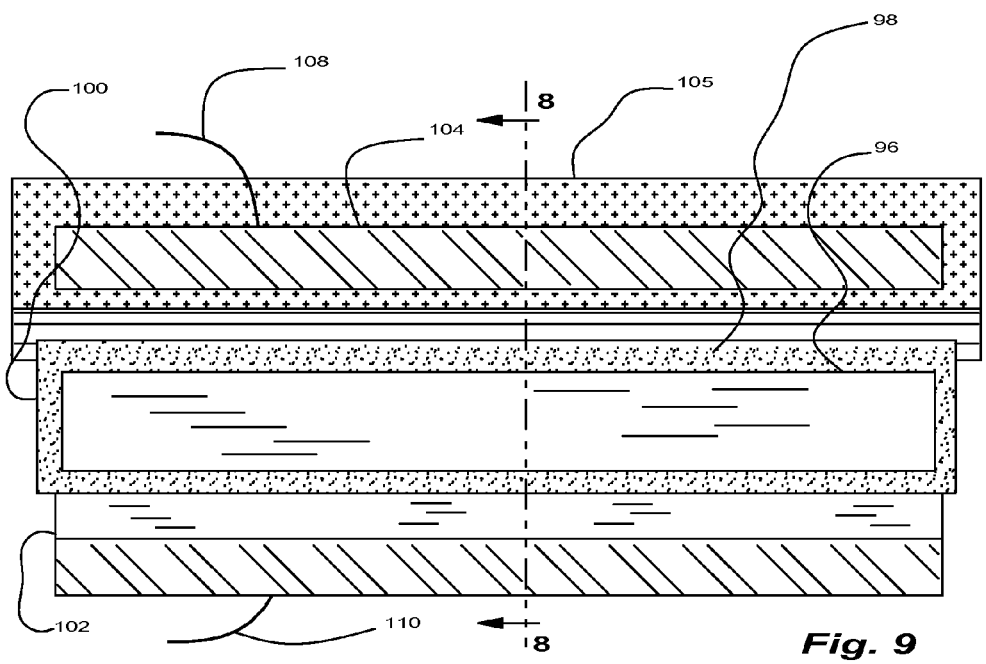

DIELECTRIC PLASMA CHAMBER APPARATUS AND METHOD WITH EXTERIOR ELECTRODES

This application is a continuation of U.S. application Ser. No. 11/668,349 filed Jan. 29, 2007, the contents of which are incorporated by this reference in its entirety for all purposes as if fully set forth herein.

BACKGROUND OF THE INVENTION

1. Field of the Invention

The invention relates in general to methods and devices for applying a non-thermal plasma treatment to objects to change the object's surface characteristics, and, more particularly, embodiments of the present invention relate to treating solid surfaces in a substantially sealed dielectric barrier discharge plasma chamber system with exterior electrodes.

2. Description of the Prior Art

The use of non-thermal plasma to modify the surface properties of many solids for many different purposes is well known. Thermal plasma generators typically operate at temperatures where most metals melt or vaporize, so they are unsuitable for use with organic polymers, and the like. Non-thermal plasma treatment of the surfaces of objects changes the electrical charge, physical and/or chemical properties of the surface. Such properties include, for example, surface tension, biocompatibility, functionality, and the like. See, for example, Murokh U.S. Pat. No. 5,798,146. Depending on the composition of the atmosphere in the region where the non-thermal plasma forms, chemical modification of the surface may be accomplished. Deposits that are only a few molecular layers thick may be formed. At high power settings, the surface of the workpiece may be etched or damaged. Various systems for generating non-thermal plasma had been previously proposed.

It is well known that when two or more electrodes are spaced apart to form a gap between them, the application of oscillating high voltage across them will, under the right conditions, cause a non-thermal plasma or glow discharge to form. The plasma forms when the breakdown voltage is exceeded. The breakdown voltage of a plasma (glow discharge) system is dependent upon the width of the gap between the electrodes, the pressure and characteristics of the atmosphere in that gap as well as the frequency of the applied voltage. Generally, the minimum voltage required to sustain the glow discharge decreases with increasingly higher frequencies. At constant atmospheric conditions, the breakdown voltage decreases as the width of the gap decreases. The breakdown voltage also decreases as the pressure of the atmosphere decreases. The breakdown voltage also depends on the nature of the gas between the electrodes. For example, at atmospheric pressure, the breakdown voltage for neon or argon filled gaps is much lower than for air filled gaps. For a given system of electrodes, gap and atmosphere, the required power density (Watts per square centimeter) is largely dictated by the purpose for which the plasma is applied to the surface. Where the surface is to be etched or otherwise physically changed, the power density is much higher than where only the electrical charge of the surface is to be altered.

Numerous non-thermal plasma generator configurations had been previously proposed. One such prior system comprises a vacuum chamber in which bare electrodes are connected to an oscillating high voltage source. See, for example, FIG. 1 where such a system is indicated generally at 10. System 10 includes a vacuum chamber 19, which is evacuated to a pressure in the millitorr range by vacuum pump 22 through vacuum line 24. A source of oscillating high voltage electrical energy 26 is connected by electrical leads 28 and 30 to a pair of bare electrodes located within chamber 19. Plasma forms within the chamber 19 between the bare electrodes. Such systems are expensive to make. The electrodes must be built into the chamber and the electrical leads carefully sealed to hold the vacuum. Expensive seals are required. Precision in construction is required, and the precision must be maintained in operation, which requires very skilled operators. Expensive two stage vacuum pumps are typically required to draw the pressure down to acceptable millitorr operating levels. Operating expenses are high because of the pumps, the maintenance, and the long cycle times, which tend to be in the order of several minutes. Such systems are typically too expensive to build to fit one particular part. They are designed as general-purpose plasma treatment generators. For this reason there is a large gap between the electrodes, which dictates that the pressure must be reduced to the millitorr range. A particular workpiece may not fit well in the chamber, so it does not receive a uniform surface treatment, or it may leave a lot of empty space in the chamber. This empty space must be evacuated at considerable operating expense. Such systems are designed to operate in a batch mode.

Dielectric barrier discharge plasma generating systems are well known. Dielectric barriers serve to promote the formation of a more uniform plasma. Dielectric barrier discharge systems are characterized by the presence of a dielectric barrier associated with at least one of the electrodes. Often the dielectric barrier is provided as a coating on one or more of the electrodes. Dielectric barriers in dielectric barrier discharge systems are typically less than approximately 0.1 inches thick, and may be as thin as approximately 10 microns or less. For purposes of illustration, the dielectric barriers illustrated in the Figs. herein are usually shown as being thicker than they actually are.

A prior dielectric barrier discharge plasma generator system is depicted diagrammatically in FIG. 2. The depicted dielectric barrier discharge system (DBD) indicated generally at 12 includes a pair of electrodes 38 and 40, connected via electrical leads 44 and 46 to a source 42 of oscillating high voltage electrical energy. Dielectric barriers 34 and 36 are interposed between at least one of electrodes 38 and 40, respectively, and the region 48 where plasma forms. The system operates at atmospheric pressure without a vacuum chamber. It is very hard to maintain a stable glow discharge between the electrodes in air, because of significant plasma instabilities. At atmospheric pressure in air, plasma has a streamer like pattern with highly non-uniform volume energy distribution. In order to sustain a uniform volume discharge at atmospheric pressure for gaps between the electrodes of about 1 centimeter (cm) and more, special air/helium mixtures, or the like, are generally required. Argon or helium may be injected into the gap where the plasma forms so as to control the atmosphere within the gap. It is practically impossible to form a uniform plasma in air at atmospheric pressure for gaps of more than approximately 5 cm. Continuous webs are often treated using a system of the type schematically depicted in FIG. 2.

Yet another previously proposed form of plasma generator is diagrammatically depicted in FIG. 3. The system depicted generally at 14 is a hybrid in that it includes a vacuum chamber 19 like the embodiment depicted in FIG. 1, and a dielectric barrier discharge configuration as depicted in FIG. 2. At least one of electrodes 38 and 40 is provided with a dielectric facing such as shown at 34 and 36, respectively. The electrodes are connected to a source 50 of oscillating high voltage by way of electrical leads 52 and 54, respectively. The chamber 19 is evacuated to a very low pressure by vacuum pump 22 through vacuum line 24. The application of oscillating high voltage electrical energy to electrodes 38 and 40 causes plasma to form in the region 56 between the electrodes.

Vacuum chambers with electrodes within the chamber in dielectric barrier discharge systems are well known, but they are expensive to buy and operate, because they typically must operate in the millitorr pressure range and at high voltages. This is because of large gaps (3 inches or more) between the electrodes that are required to accommodate a variety of different workpieces. Also, the construction of in-chamber electrode systems is expensive. The chambers with internal electrodes are generally too expensive to custom build to fit a single part, so they are made big enough to accommodate a variety of different parts or a plurality of parts of the same configuration. They require expensive two stage pumps to bring the pressure down into the millitorr range. Cycle times are in the nature of minutes, and they are usable only in a batch processing mode.

Some in-chamber dielectric barrier discharge systems have been proposed for single purpose operations. See, for example, DeVries et al. US 2006/0147648, Pub. Jul. 6, 2006. De Vries proposes the use of a dielectric barrier discharge system wherein a special gas atmosphere (for example, air, argon, nitrogen, oxygen, carbon dioxide, ammonium, common precursors, etc.) is confined within a chamber around a thermoplastic film. The surface of the thermoplastic film is treated with plasma as it is transported past a set of electrodes. The electrodes on one side are coated with a dielectric, and the film is supported by the bare electrode on the other side. The chamber is at atmospheric pressure and vents directly to the surrounding atmosphere, although it is mentioned without amplification that the process may be operated below atmospheric pressure such as between 100 mbar and 1 bar (approximately between 75 and 750 Torr) pressure. It is not clear how the system could be modified to operate at reduced pressures. The gap between the electrodes and the workpiece film is described to be in the range of 0.1-5 millimeters, which is indicative of operation at or near atmospheric pressure.

Dielectric barrier discharge systems had been proposed for the treatment of gases flowing axially within a stationary dielectric tube. See, for example, Shiloh et al. U.S. Pat. No. 6,245,299. Shiloh discloses a series of electrode sets, each set being axially spaced from its neighbors, all of which are arrayed along a stationary dielectric tube. The stationary dielectric tube is located between the electrodes of each set so that a non-thermal plasma is caused to form inside of the tube at the sites where the sets of electrodes are located. A polluted gas stream flows through the tube and is serially treated by plasma as it passes each set of electrodes. The composition of the polluted gas stream is changed as it passes through the plasma. A similar stationary dielectric barrier discharge system for treating a flowing gas stream is described in Lazarovich et al. U.S. Pat. No. 6,685,803.

Hammerstrom et al. U.S. Pat. No. 6,455,014 discloses a non-thermal plasma generating blanket that may be draped over a contaminated surface. The blanket is in the form of a dielectric barrier discharge system.

Jacob U.S. Pat. No. 6,342,187 discloses the use of a number of dry sterilization procedures, one of which is described as plasma glow. The devices that are said to be sterilized include small elongated cylindrical medical devices such as fiber optics devices. The teaching appears to be that such elongated devices should be placed in some outside container, and the sterilization procedure applied in that container in a batch procedure.

Nakamura et al. U.S. Pat. No. 6,489,585 describes the dielectric barrier discharge plasma treatment of the surface of a moving glass substrate for purposes of cleaning the surface. The plasma is generated in a treatment chamber.

A typical prior plasma generating system might require, for example, a source of electrical energy that provides 1,000 Volts (1 KV) and a current (for example, 1.0 Amp) to establish a glow discharge (plasma) in a vacuum with a gap between the electrodes of about 4 inches. Dielectric barrier discharge at atmospheric pressure might require 10 KV and 0.1 Amp to create plasma in a gap of less than one-quarter inch. Breakdown voltages vary with the pressure. For example, typical breakdown voltages for about a 1 centimeter (cm) gap at different pressures are shown in the following table.

TABLE 1

| Breakdown Voltages (KV) for 1 cm gap | | |
| --- | --- | --- |
| Pressure (Torr) | Air | Argon |
| 760 | 30 | 3 |
| 100 | 6 | 1 |
| 10 | 1 | 0.3 |
| 1 | 0.3 | 0.2 |

The effect of the composition of the atmosphere on the breakdown voltage decreases as the pressure is reduced.

These and other difficulties of the prior art have been overcome according to the present invention.

BRIEF SUMMARY OF THE INVENTION

The present invention has been developed in response to the current state of the art, and in particular, in response to these and other problems and needs that have not been fully or completely solved by currently available non-thermal plasma generator systems and methods. The present invention effectively resolves at least the problems and shortcomings identified herein. In particular, embodiments of the present invention provide a dielectric barrier discharge plasma generator for the treatment of solid surfaces wherein at least a plasma generating electrode is positioned outside of and separately moveably from a substantially sealed dielectric chamber. The walls of the chamber comprise dielectric material to provide a dielectric barrier positioned between the electrodes and the workpiece. A workpiece is placed or occurs within the dielectric chamber. In various embodiments, the dielectric chamber and the workpiece may be one and the same, or the workpiece may be fully or partially enclosed within the dielectric chamber. A plurality of separate dielectric chambers may be provided. A gap is provided within the dielectric chamber in which non-thermal plasma may form. An atmosphere control system is provided to control the atmosphere within the chamber. A transport system is provided for moving the electrodes and the dielectric chamber relative to one another. Plasma generating electrical power is supplied to the electrode(s). When the breakdown voltage is achieved in the plasma zone, non-thermal plasma forms. The non-thermal plasma stays in a plasma zone between the electrodes during this relative movement. The solid surfaces that are treated with non-thermal plasma are moved with the dielectric chamber. Solid surfaces include those that are not fluid. Fluids assume the shape of the container that confines them. Solids are capable of sustaining their own shape. Solids include gels and sols that are capable of sustaining their shapes without support. Solid surfaces are not limited to surfaces of any particular texture. Woven materials and mats (particularly filters) have solid surfaces, as do particulate and granular materials. Many smooth surfaces are solid, as are many permeable and impermeable surfaces. The system is particularly adapted to continuous operations, which permits automation of the process, and the use of non-thermal plasma treatment in the mass production of plasma treated solid surfaces, which results in substantial economies of operation. Production rates go up by several orders of magnitude when operations are improved from batch to continuous.

In certain embodiments, a dielectric barrier discharge plasma generator comprises a dielectric chamber. The generator is adapted to treating a solid surface within the dielectric chamber with non-thermal plasma to cause modifications of that surface. This dielectric chamber comprises dielectric material and is capable of being substantially sealed. Many dielectric materials are slightly permeable to one or more gases. It is not necessary that the dielectric chambers hold a constant level of vacuum indefinitely. It is sufficient that the desired level of rough vacuum be held within the necessary operating tolerances for the period of treatment. In one embodiment the vacuum pump system remains attached during the plasma treatment. In another embodiment the vacuum pump system is disconnected during the plasma treatment. This dielectric material serves as the dielectric barrier in the dielectric barrier discharge generator. The dielectric material is generally between at least one of the electrodes and the plasma zone. The dielectric chamber is adapted to being substantially sealed, and to confining an atmosphere therein. An atmosphere control system serves to control the atmosphere as to pressure or composition, or both, to a predetermined value. When the pressure of the atmosphere is reduced, a rough vacuum (approximately 0.1 to 100 torr) is sufficient to allow easy generation of desired non-thermal plasma. At least one or two electrodes are located outside of the dielectric chamber. The electrode(s) are located outside of, separate from, and in plasma generating relationship to the dielectric chamber. These electrodes are operatively connected to a source of plasma generating electrical power. When such power is applied to the electrodes a solid surface modifying non-thermal plasma is generated in the dielectric chamber. A transport or movement system establishes relative motion between the electrode and the dielectric chamber. The dielectric chamber serves to confine a plasma zone therein when the dielectric chamber or a portion thereof is adjacent to the electrodes. The dielectric material is positioned generally between at least one of the electrodes and the plasma zone. The electrodes, when activated by the electrical power, cause non-thermal plasma to form in the plasma zone. The plasma zone remains substantially stationary relative to the electrodes. The dielectric chamber carries the solid surface through the plasma zone so that the solid surface is substantially stationary relative to the dielectric chamber.

In some embodiments of this dielectric barrier discharge plasma generator the solid surface to be treated is part of the dielectric chamber. That is, the dielectric chamber and the workpiece are the same. For example, when the dielectric chamber comprises a length of hollow tubing or an empty container, the solid surface comprises an inside wall of the hollow tubing or container. In certain embodiments, the transport system is adapted to move the length of hollow tubing or empty container past stationary electrodes. A plasma zone forms within the dielectric chamber adjacent to the electrodes. The plasma zone remains adjacent the electrodes as the tubing moves past the electrodes. The dielectric tubing comprises a dielectric material and has an inside diameter of less than approximately 10 millimeters, or 5 millimeters, or less, and an aspect ratio of at least 10 to 1, or 100 to 1 or greater.

Embodiments of the present invention are particularly suitable for use in treating the inside surfaces of lengths of hollow dielectric tubing for sterilization, surface functionalization, surface tension modification, or the like. The interior surface of the tube and the surface of anything within the tube are treated by the plasma. The dielectric chamber may serve alternatively or simultaneously as both the workpiece and as a holder for a second workpiece. For example, if a second dielectric tube is positioned within the hollow interior of a dielectric tube and pressure is reduced within both tubes, plasma will treat the surface of the inside wall of the outside dielectric tube and the exterior surface of the inside tube. If pressure is reduced only within the interior of the inside tube, only the interior surface of the inside tube will be treated. Also, providing different atmospheric conditions (e.g. gas pressure and/or gas compositions) within the two tubes may cause alternative treatments of the inside and outside surfaces of the inner tube with a single pass through a plasma zone. Hollow tubing is used in many medical procedures. Treatments of surfaces in accordance with the present invention are particularly desirable in such applications.

When a dielectric chamber is generally elongated and of a substantially constant lateral cross-section, the set of electrodes may, for example, have a generally arcuate configuration with a central opening sized and shaped so that it permits the elongated dielectric chamber to pass axially therethrough with just enough clearance between the inner surfaces of the electrodes and the outer surface of the elongated dielectric chamber to permit the chamber to slide easily relative to the set of electrodes. This configuration is particularly suited to a situation where a workpiece is an elongated cylindrical tube, but is also applicable to chambers of any length, but with substantially constant cross-sections. Where the lateral cross-section of a dielectric chamber is irregular but generally axially constant, the electrodes may be shaped to conform to the irregular cross-section. The electrodes are inexpensive to make and replace, because they are not within or permanently affixed to the dielectric chamber. Likewise, they may be adjusted and positioned independent of the dielectric chamber as may be required or desired for a particular operation. The electrodes may be planar, angular, arcuate, compound, or the like, as may be desired.

The use of an elongated workpiece permits long lengths to be treated very quickly. Lengths with aspect ratios (length to internal diameter) of greater than 100 to 1 may be quickly and conveniently treated with plasma. Lengths of longer workpieces may be selectively treated. For example, if a 100 foot length of treated tubing is desired, and a 1,000 foot long reel of the tubing is available, the entire reel can be quickly evacuated to a pressure of from approximately 1 to 100 Torr, and only the first 100 foot length is treated. Millimeter sized tubing may be easily treated. Relatively flexible tubes may be treated, because the pressure is not reduced to a level where the tube collapses. Pressures in the millitorr range would collapse many of the tubes that are particularly benefited by this plasma treatment.

According to one embodiment, a rough vacuum (0.1 to 100 Torr), rather than a gas such as argon or neon, is used to promote the formation of plasma in elongated hollow tubes. With a vacuum, there is no risk that contamination will be introduced with the gas. This is particularly significant for medical applications. The use of a vacuum in medical applications is usually preferable to the use of an inert gas because the freshly charged inside surface of the tube will likely attract and hold any trace contaminants that are present in the gas. If air is drawn into the tubing through filters to purge contaminants from the inside of the tubing before a rough vacuum is drawn, there will be substantially no particulates or other contaminants present when the treatment takes place. For the same reason, when the rough vacuum is released, air or other fluid is let back into the treated tube through appropriate filters.

Where it is desired to coat the inner surface of, for example, a hollow tube, with some material, for example, a material that exhibits a therapeutic effect, a gas phase reagent that provides the desired material when subjected to a plasma is introduced into the hollow tube and treated with plasma. Both the inner wall of the tube and the reagent confined therewithin are treated by the plasma.

In some embodiments, the solid surface is part of an object that is not a part of the dielectric chamber. In such embodiments, at least the solid surface that is to be treated with plasma to modify it is within the dielectric chamber.

In some embodiments, the dielectric chamber is one of a plurality of separate dielectric chambers. Solid surfaces in separate dielectric chambers may be treated individually in a continuous operation. In certain embodiments the dielectric chamber comprises a shipping, handling and storage container for an object on which the solid surface occurs.

In certain embodiments, one or more of the electrodes is irregular shaped and is adapted to generate non-thermal plasma in a pattern that is approximately determined by the irregular shape of the electrode. The irregular may be fixed or controllably variable, as desired.

According to an additional embodiment, at least one of the electrodes in a set of electrodes is irregular shaped and generates a plasma to modify the surface properties of a workpiece located in the dielectric chamber in a pattern that is determined by the irregular shape of the electrode. Typically, where the workpiece is irregular in shape, the electrode is shaped to provide an approximately uniform plasma treatment across the entire surface of the workpiece. In some circumstances, it may be desirable to apply a plasma treatment non-uniformly to a regular shaped surface. The use of an irregularly shaped electrode permits such non-uniform plasma application.

In some embodiments, particularly where the solid surface is too large to all be treated at one time, the dielectric chamber includes a plurality of plasma zones. The electrodes and/or dielectric chamber are advanced relative to one another until the entire solid surface has passed through a plasma zone.

In some embodiments, only one electrode is employed.

Embodiments of the present invention are particularly well suited to automated and continuous production operations. For example, providing regulating indicia in association with a dielectric chamber permits the regulation of at least one of the operating parameters in the plasma zone. For example, the parameters of the plasma generating electrical power, the shape and size of the plasma zone, the length of the exposure time in the plasma zone, the characteristics (pressure and/or composition) of the atmosphere, or the like, responsive to information derived from the regulating indicia for that particular dielectric chamber. The regulation of the operating parameters can be accomplished on the fly without stopping the relative movement between the dielectric chambers and the electrodes. The regulating indicia can be read by conventional sensors and computer input devices, and the information thus derived from the regulating indicia processed into operating instructions and applied through conventional computerized controls. A plurality of separate sealed dielectric chambers containing separate surfaces to be treated are prepared and presented serially substantially one by one to one or more electrodes for plasma treatment. The treatment each separate solid surface receives is tailored to that surface even though the overall operation is substantially continuous.

According to an embodiment, the system is operated with the atmosphere in the dielectric chamber under a rough vacuum of approximately 0.1 to 100 Torr, in additional embodiments, approximately 1 to 100, and 1 to 10 Torr. This pressure is sufficient to allow a uniform plasma to form, but not low enough to cause the collapse of small diameter dielectric tubes or other dielectric chambers, or to require expensive vacuum pumps and equipment.

A source of oscillating (approximately 10 to 100 KHz) high voltage (approximately 50 to 0.1 or 10 to 1 KV) plasma generating electrical power is provided to supply the necessary electrical power to the electrodes.

Making the electrodes separable from the dielectric chambers permits the use of multiple dielectric chambers with one set of electrodes. It also substantially reduces the costs of producing both the chambers and the electrodes. Particularly for purposes of mass production, a large number of interchangeable dielectric chambers can be loaded with workpieces. The atmospheres within each chamber can be adjusted to desired values of pressure and composition before the chamber is mated to a set of electrodes. The pre-prepared dielectric chambers may be placed one by one in plasma treatment association with the electrodes. Conveying such chambers past one or more sets of electrodes at a continuous rate or in a regular stop and go motion permits the automation of the operation for purposes of mass production.

In those embodiments where separate individual chambers are individually loaded with workpieces, the dielectric chambers may be advantageously shaped to accommodate the specific workpieces, and as much as 80 to 90 percent of the volume inside of a particular dielectric chamber is occupied by the workpiece. Such a void volume of 10 to 20 percent reduces, for example, the load on the vacuum pump and cycle times, and minimizes the consumption of reagents, if any are employed. The generally separate external electrodes may also be shaped to accommodate the specific chamber-workpiece assemblies. The dielectric chamber walls and the electrodes may be shaped to provide approximately a constant gap between the surface of the workpiece and the electrode. The use of external separate electrodes allows the electrodes to be manufactured inexpensively, as needed, to accommodate different shaped chamber-workpiece assemblies. Cooling may be provided for the electrodes where they are subjected to continuous use. Typically, cooling fluid (liquid or gas) is used to cool the electrodes.

The present invention provides a non-thermal plasma treatment operation that is flexible enough to provide an optimum solution for each particular case.

To acquaint persons skilled in the pertinent arts most closely related to the present invention, an embodiment of a dielectric barrier plasma generator that illustrates the best mode now contemplated for putting the invention into practice is described herein by, and with reference to, the annexed drawings that form a part of the specification. The exemplary plasma generator and method are described in detail without attempting to show all of the various forms and modifications in which the invention might be embodied. As such, the embodiments shown and described herein are illustrative, and as will become apparent to those skilled in the arts, can be modified, changed, and combined in numerous ways within the scope and spirit of the invention, the invention being measured by the appended claims and not by the details of the specification or drawings.

Other objects, advantages, and novel features of the present invention will become more fully apparent from the following detailed description of the invention when considered in conjunction with the accompanying drawings, or may be learned by the practice of the invention as set forth herein.

BRIEF DESCRIPTION OF THE DRAWINGS

The present invention provides its benefits across a broad spectrum of plasma generator systems and methods. While the description which follows hereinafter is meant to be representative of a number of such applications, it is not exhaustive. As those skilled in the art will recognize, the basic apparatus and method taught herein can be readily adapted to many uses. This specification and the claims appended hereto should be accorded a breadth in keeping with the scope and spirit of the invention being disclosed despite what might appear to be limiting language imposed by the requirements of referring to the specific examples disclosed.

Referring particularly to the drawings for the purposes of illustrating the invention and its presently understood best mode only and not limitation:

FIG. 4 is a generalized diagrammatic cross-sectional view of an embodiment of the present invention wherein the atmosphere within a chamber is controlled, the walls of the chamber are composed of dielectric materials, the electrodes are located outside of the chamber, and a workpiece is placed within the chamber.

FIG. 5 is a diagrammatic cross-sectional view of an embodiment of the present invention taken along line 5-5 in FIG. 7 wherein the dielectric barrier and the workpiece are one and the same. The barrier-workpiece comprises, for example, an elongated generally cylindrical tube, the walls of which are composed of a dielectric material. A set of annular electrodes generally forms a ring around the tube, and non-thermal plasma is generated within the tube so the inside surface of the tube, and any other surfaces within the tube, are treated. In the embodiment chosen for illustration, the electrodes are also covered with a dielectric material, primarily for wear and safety purposes, although this covering does influence the plasma somewhat. The thickness of the optional dielectric covering on the electrodes is exaggerated for purposes of illustration.

FIG. 6 is a diagrammatic cross-sectional view taken along line 6-6 in FIG. 5.

FIG. 7 is a diagrammatic cross-sectional view taken along line 7-7 in FIG. 5.

FIG. 8 is an exploded, generalized, diagrammatic cross-sectional view taken along line 8-8 in FIG. 9 of an embodiment of the present invention wherein the geometric configurations of the electrodes are adapted to accommodate the irregular geometric configuration of a dielectric chamber-workpiece assembly. The thickness of the dielectric coating and the spacing of the elements have been exaggerated for purposes of illustration.

FIG. 9 is a generalized diagrammatic cross-sectional view taken along line 9-9 in FIG. 8.

DETAILED DESCRIPTION OF THE PRESENTLY PREFERRED EMBODIMENTS

Figure 1:
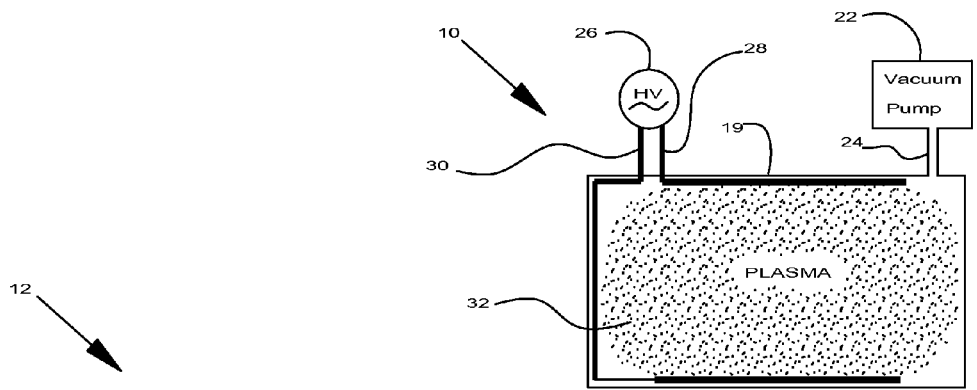
FIG. 1 is a generalized diagrammatic cross-sectional view that generally depicts one type of prior art non-thermal plasma generating device wherein plasma is generated between bare electrodes inside of an evacuated chamber.

Referring now to the drawings wherein like reference numerals designate identical or corresponding parts throughout the several views. It is to be understood that the drawings are diagrammatic and schematic representations of various embodiments of the invention, and are not to be construed as limiting the invention in any way. The use of words and phrases herein with reference to specific embodiments is not intended to limit the meanings of such words and phrases to those specific embodiments. Words and phrases herein are intended to have their ordinary meanings, unless a specific definition is set forth at length herein.

Figure 2:
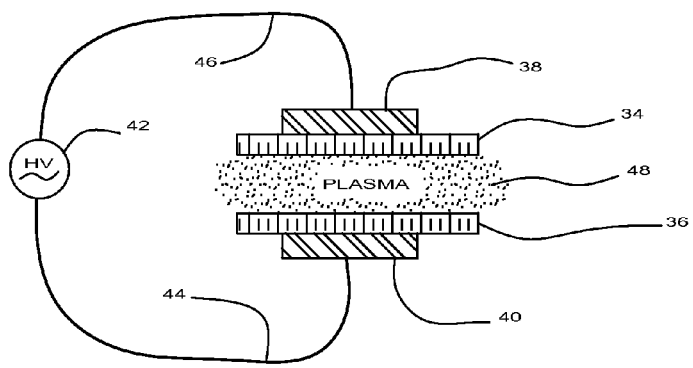
FIG. 2 is a generalized diagrammatic cross-sectional view that generally depicts another type of prior art non-thermal plasma generating device wherein plasma is generated at approximately atmospheric pressure between dielectric barriers that separate the electrodes from the region where the plasma is generated. This prior art type of plasma generation is sometimes described as a dielectric barrier discharge plasma generator.
Figure 3:
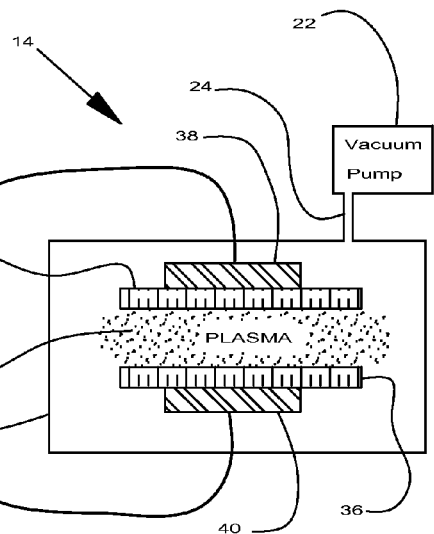
FIG. 3 is a generalized diagrammatic cross-sectional view that generally depicts a third type of prior art non-thermal plasma generating device, which is a hybrid of the types of prior art devices depicted in FIGS. 1 and 2. The entire dielectric barrier discharge plasma generator of FIG. 1, including the electrodes, is placed inside of an evacuated chamber.

Referring particularly to the drawings, there is illustrated generally at 10, 12, and 14, in FIGS. 1, 2, and 3, respectively, prior art plasma generators as previously described hereinabove.

With particular reference to FIG. 4, there is illustrated generally at 16 an embodiment of the present invention where a dielectric chamber 66 is mounted between a single set of electrodes, the individual ones of which are indicated at 62 and 64. A source of oscillating high voltage is provided at 68, and is connected to the electrodes through electrical leads 70 and 72, respectively. The atmosphere within the dielectric chamber 66 is controlled by an atmosphere control system 58, and applied to the interior of dielectric chamber 66 through conduit 60. When appropriate electrical energy is applied to electrodes 62 and 64, a plasma forms inside chamber 66 in region 74. The atmosphere control system may serve to flush, evacuate, supply reactants, supply a non-air atmosphere, or the like, to the dielectric chamber 66. Dielectric chambers according to the present invention are considered to have an atmosphere when there is enough gas, regardless of its composition, in chamber 66 to produce a pressure reading of at least approximately 0.1 Torr. Dielectric barriers 63 and 65 are optional, used for example, for protecting the electrodes and the dielectric chamber from wear. The dielectric walls of chamber 66 are generally sufficient to cause the formation of the desired uniform plasma within chamber 66. For purposes of clarity of illustration, no workpiece is illustrated in FIG. 4.

FIGS. 5, 6, and 7 are directed to an embodiment wherein the workpiece and the dielectric chamber are the same, as indicated generally at 18. The combined workpiece-dielectric chamber is defined by an elongated generally cylindrical hollow dielectric tube 76, which has a substantially constant cross-section and an inner surface 78. A generally annular set of electrodes 84 consists of two electrodes separated by insulating air gaps 88. The internal diameter of the set of electrodes 84 should be large enough that tube 76 is enabled to pass unobstructed therethrough along its longitudinal axis. Typically, the clearance between the exterior of tube 76 and the interior of the annular electrode set 84 is less than approximately 1.0, and in an additional embodiment, less than approximately 0.1 inches. Tube 76 is guided into the interior of the annular electrodes 84 by collar 86. Collar 86 is composed of non-conductive material and is flared radially outwardly to receive the tube 76. An atmosphere control system (not shown) is applied to regulate the atmosphere in chamber 80. Source 90 of oscillating high voltage energy is connected through electrical leads 92 and 94 to the respective electrodes in electrode set 84. The interior annular surface 78, which surrounds chamber 80, serves to confine the atmosphere that is established by the atmosphere control system in region 82. The wall of tube 76 acts as a dielectric barrier for purposes of generating plasma in a dielectric barrier discharge system. A plasma forms in region 82 and extends in the chamber 80 typically for several inches on either side of the electrodes. The plasma treats the interior annular surface 78 of tube 76. The nature of that treatment and the properties of the resultant treated workpiece surface are determined by at least the power density of the applied electrical energy, the length of the exposure of the surface to the plasma, and the composition and pressure of the atmosphere in the region 82. The results of the non-thermal plasma treatment may range from merely changing its surface tension by charging the surface to physically altering the shape of the surface. The chemical characteristics of the surface may be changed by the removal or addition of various radicals, or the like. The annular set of electrodes 84 may be fastened together as one unit so that the tube must be inserted beginning at an end thereof. Alternatively, the set of electrodes may be constructed so that the individual electrodes are separable from one another to allow the lateral insertion of a tube. The electrodes may be coated with a dielectric as shown, or not coated, as may be desired. In a further embodiment the electrodes may be planar rather than arcuate.

With particular reference to FIGS. 8 and 9, a single purpose dielectric barrier discharge plasma generator, indicated generally at 20, is shown. For purposes of clarity of illustration, the associated atmospheric control system is not shown. The functions of the atmospheric control system are as previously described, for example, with reference to the embodiments of FIGS. 4 through 7. A dielectric barrier chamber 100 is configured to conform to the shape of workpiece 96. Workpiece 96 may have a shape that is regular, irregular, angular, arcuate, or some combination thereof, as may be desired.

When electrodes 102 and 104 are fully assembled to dielectric barrier chamber 100, the gap 112 may or may not be substantially closed. The electrodes 102 and 104 are separated or insulated so that there is no arc or short circuit therebetween. Electrodes 104 and 102 are connected through electrical leads 108 and 110, respectively, to oscillating high voltage power source 106. The electrodes conform to and fit over the outer surface of dielectric barrier chamber 100. An insulating layer 105 on electrode 104 is illustrated. This insulative layer 105 is optional. It may or may not be used. The chamber 100 is separated somewhat from the work piece 96 to provide plasma zone 98 in which a non-thermal plasma forms. In an embodiment, the electrodes separate to allow the insertion of the dielectric chamber 100 between them.

In operation, chamber 100 is opened, workpiece 96 is inserted, the characteristics of the atmosphere in the chamber are adjusted by an atmosphere control system (not shown), the chamber is sealed, the chamber is mated to the set of electrodes, and source 106 is activated to provide oscillating high voltage electrical power to the electrodes. Upon the application of electrical power to the electrodes 102 and 104, a plasma forms in plasma zone 98 and treats the outer surface of workpiece 96 in a substantially uniform pattern. The treated workpiece is recovered by opening the set of electrodes and the chamber, and removing the treated workiece. If desired, the treated workpiece 96 may be stored in chamber 100 until it is used. In this case, the chamber 100 is generally disposable.

Typically, but not necessarily, the pressure of the atmosphere in a dielectric chamber according to the present invention is reduced. In some circumstances it may be desirable to use, for example, an atmosphere of argon, helium, or neon, mixtures thereof, or the like, at or near ambient atmospheric pressure. This may be desirable, for example when a reactant is present in the atmosphere.

Carrying out a typical cycle for treating a separate workpiece with plasma according to the present invention includes the steps of placing the workpiece in a vacuum chamber that has dielectric walls. The chamber is sealed. A single stage vacuum pump is connected to the vessel. The vessel is typically evacuated to a pressure of from approximately 100 to 0.1, and, in a further embodiment, approximately 30 to 1 Torr. At least one set of electrodes is positioned adjacent to but outside of the vessel so that the dielectric walls of the chamber are between the electrodes and the region within the vacuum chamber where the plasma forms. An oscillating high voltage source is connected across the electrodes, and a plasma is formed. The plasma is maintained for a period of time sufficient to effect the desired change to the surfaces of the workpiece, typically, from approximately 1 sec to 1 min. The vessel is opened, and the treated workpiece is removed.

According to a further embodiment, the chamber is separable from the set of electrodes so that several chambers may be prepared at a remote location and rapidly presented to the electrodes one by one for plasma treatment. The use of exterior separable electrodes provides what is inherently a batch operation with many of the advantages of a continuous operation. For purposes of efficiency, the shape of the chamber is tailored to at least the general shape of the workpiece. Such tailoring allows the void volume in the chamber to be less than approximately 30 percent, and in an embodiment, less than approximately 20 percent of the total volume of the chamber. Void volumes of less than 10 percent are desirable. Reducing the void volume minimizes both the energy and the time that the vacuum pump uses in evacuating the chamber, and the necessary capacity of the pump.

Figure 11:
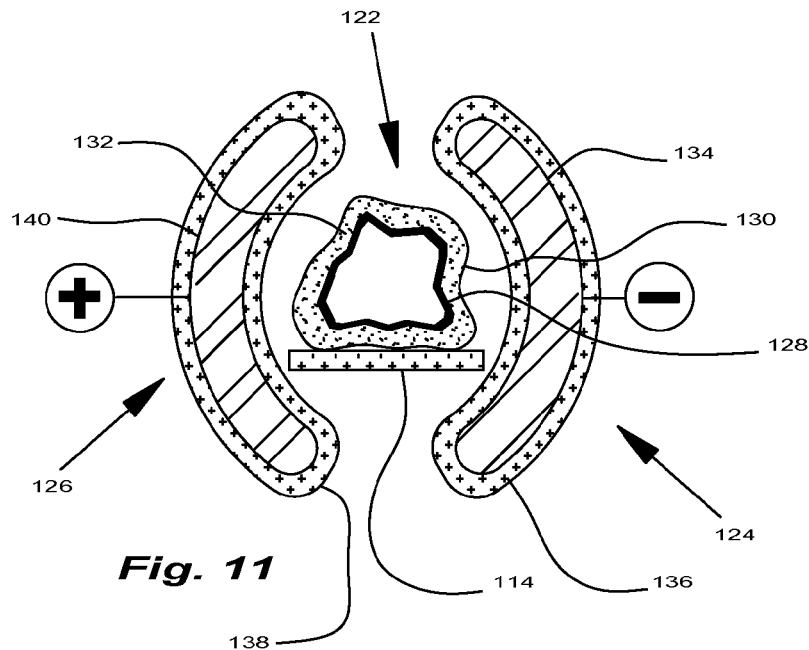
FIG. 11 is a cross-sectional view taken along line 11-11 in FIG. 10.
Figure 10:
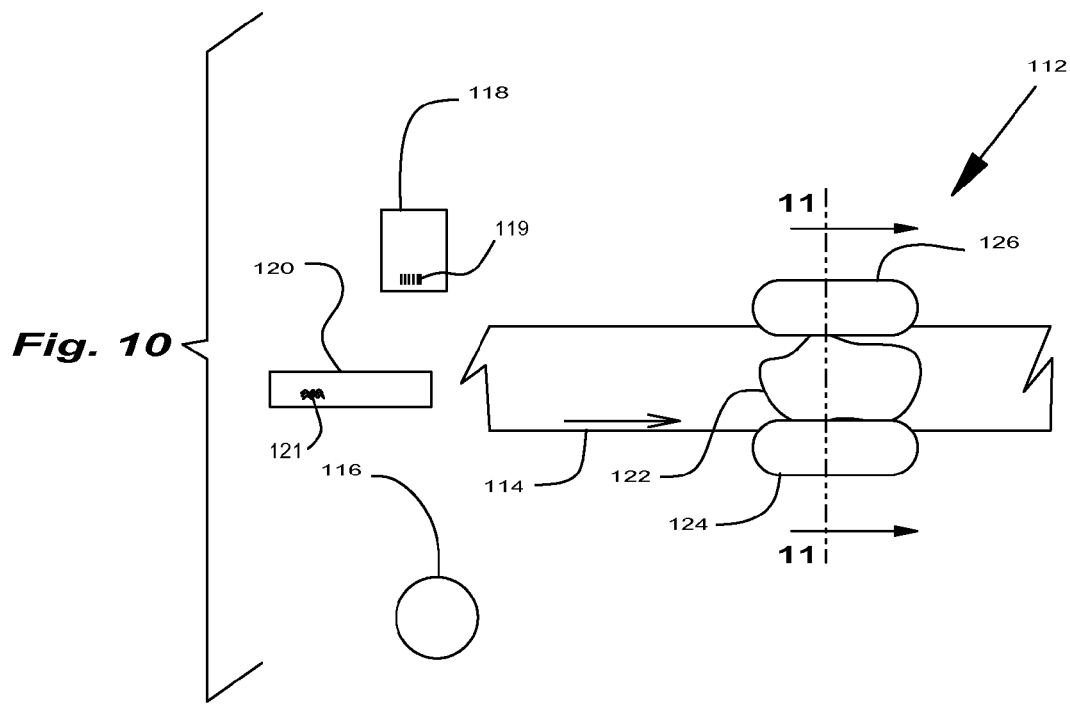
FIG. 10 is a generalized diagrammatic plan view of a continuous system according to the present invention wherein different shaped dielectric chamber-workpiece assemblies are conveyed past a stationary set of electrodes.

With particular reference to FIGS. 10 and 11, there is indicated generally at 112 a production operation for the non-thermal plasma treatment of workpieces pre-packaged in individual sealed dielectric chambers. The atmospheric conditions of, for example, pressure and composition are determined by the conditions within the individual chambers, and they need not be the same for all of the dielectric chambers employed in the same production run. A conveyor belt 114 is adapted to movingly support dielectric chamber-workpiece combinations such as are indicated at 116, 118, 120, and 122 for movement past a pair of plasma generating electrodes 124 and 126. The rate of movement past the electrodes is selected so that the desired plasma treatment is applied to a workpiece, a typical example of which is depicted at 128. A dielectric chamber 130 is provided, which in the illustrated embodiment generally conforms to the shape of workpiece 128. The dielectric barrier formed by the walls of dielectric chamber 130 is spaced from the surface of the workpiece so that plasma 132 forms in the plasma zone between the two. The characteristics of the atmosphere in the plasma zone between the workpiece and the dielectric chamber 130 are such that the breakdown voltage is much less in this region than it is in the open air outside of the dielectric chamber-workpiece 122 between the electrodes. The system is operated at such a level of oscillating voltage that plasma 132 forms in the plasma zone, but not in the open air between the electrodes. The metallic electrodes 140 and 134 are illustrated as being coated with dielectric material 138 and 136, respectively. Such coatings are desirable for safety purposes, but are not necessary. The electrodes are illustrated as being arcuate, but planar shaped electrodes are generally satisfactory. Various conventional heat transfer mechanisms and procedures (not shown) may be employed to cool the electrodes, as desired. In the embodiment chosen for illustration, there is one workpiece 128 associated with the dielectric chamber 130.

As will be understood by those skilled in the art, several workpieces may be enclosed within one dielectric chamber 130, if desired. For example, a kit containing several items that are required for a particular medical procedure may be enclosed in a single dielectric chamber. The parameters of the system are adjusted to provide sterilization for the items in the kit. The dielectric chamber may also serve as the shipping and storage container for the kit. Separate individual solid objects such as, for example, pellets, pills, short filaments, machine elements, or the like, can be loaded into a dielectric chamber in the form, for example, of a tube or tray and carried by that dielectric chamber through a plasma zone. The solid surfaces of such discrete solid objects that are exposed to plasma are thus treated in the plasma zone.

The dielectric chamber may be the same as the workpiece. For example, the inside walls of small dielectric bottles may be sterilized or otherwise treated in a continuous operation according to the present invention. Where, for example, empty bottles or vials, or empty elongated tubes are treated, the void volume is approximately 100 percent.

In operation, the individual dielectric chamber-workpiece units (116, 118, 120, and 122) may be treated in a continuous operation, but with at least power densities individually tailored to each such unit. The provision of identifying indicia, typical ones of which are indicted at 119 and 121, associated with each such unit allows the power parameters to be adjusted responsive to the identifying indicia on that unit. Such identifying indicia include, for example, shape, weight, temperature, color, size, bar code, radio frequency identification, combinations thereof, and the like. Conventional sensors (not shown) associated with the plasma treatment system are adapted to detect the identifying indicium that is associated with a particular unit, and transmit that identification data to a central processing unit. The central processing unit is adapted to processing the data and instructing the system to adjust at least the power density to provide each unit with plasma at the desired power density. The sensing and adjusting are accomplished on-the-fly without interrupting the flow of the units through the system. Other operating parameters may be similarly adjusted, as desired. The computerized control of the operating parameters of the system makes use of conventional computer control system components and programs. In those operations where the dielectric chamber-workpieces are all substantially the same there is generally no need to adjust the power density.

For purposes of illustration, the dielectric coatings on the electrodes (for example, 34, 36, 63, 65, 86, 105, 136, and 138) have been shown as being relatively thick. In practice, they are generally relatively thin, usually less than approximately a tenth of an inch in thickness.

Figure 13:
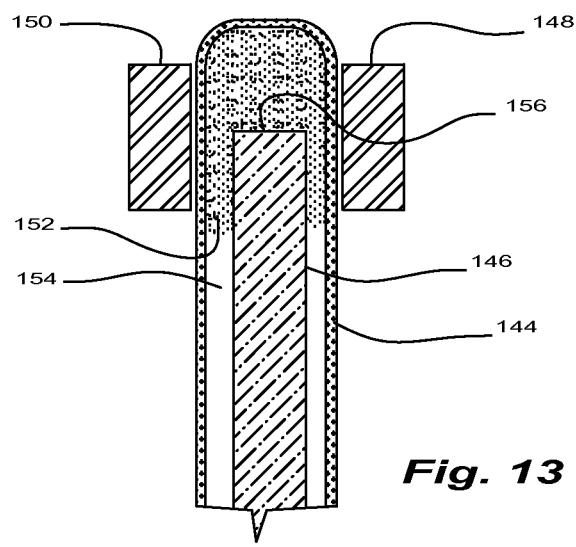
FIG. 13 is a generalized diagrammatic cross-sectional view taken along line 13-13 in FIG. 12.
Figure 12:
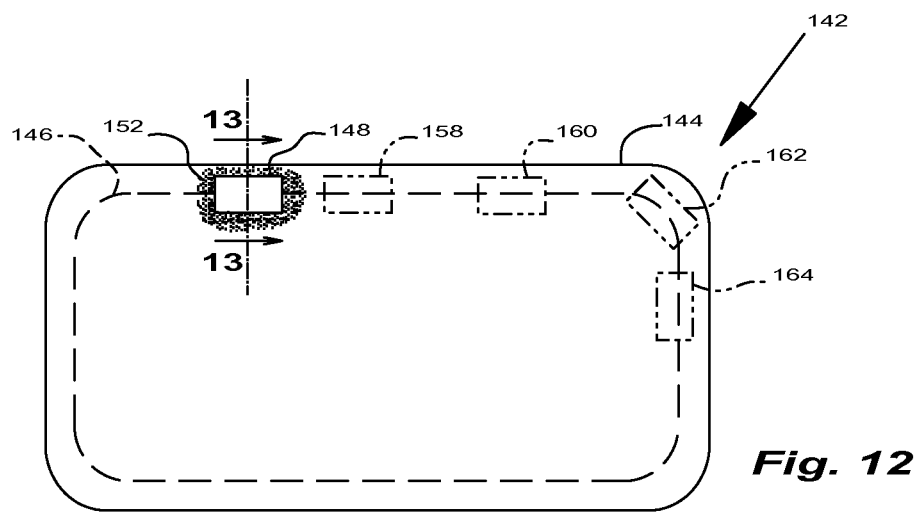
FIG. 12 is a generalized diagrammatic plan view of an incremental scanning system according to the present invention wherein parts of the edge of a relatively large workpiece encased within a sealed dielectric chamber is treated incrementally with non-thermal plasma one region at a time until the entire periphery of the workpiece has been treated. The dielectric-chamber workpiece and the electrodes are moved relative to one another to move the plasma treatment around the entire periphery of the work piece.

With particular reference to FIGS. 12 and 13, there is indicated generally at 142 an incremental plasma treatment system wherein a relatively large planer workpiece 146 is positioned inside of a sealed individual dielectric chamber 144. The atmosphere within the interior 154 of chamber 144 is adjusted as desired. For example, in an embodiment interior 154 is evacuated to a rough vacuum of approximately 1 to 10 Torr. Electrical power is applied to the exterior electrodes 148 and 150 to form plasma 152 within dielectric chamber 144 in the vicinity of the electrodes. The plasma zone surrounds edge 156 and the adjacent sides of workpiece 146. Relative motion is established between the electrodes and the dielectric chamber so that the electrodes advance relative to the edge of the workpiece as indicated at 158, 160, 162, and 164. The entire edge of the workpiece thus passes through and is treated in the plasma zone. Typical large workpieces, for example, include windshields and construction panels where the surface properties of the edges of the workpiece must accommodate bonding preparations such as, for example, adhesives. Construction panels that are benefited by treatment according to the present invention include, for example, structural and cosmetic composite panels for use in air, space, ground vehicles, and the like.

The chamber can be made inexpensively, for example, by molding, casting, or the like, so it can be used once and discarded, if desired. A one time use chamber may be molded around the workpiece and evacuated all at the same time, if desired. The chamber may also serve as the storage and shipping container for the workpiece. The chamber is inexpensive enough to make that it is economically feasible to destroy it when it is opened to retrieve the treated part. Reusable chambers may be used, if desired. Reusable chambers may, for example, be shaped to enclose only the part of the workpiece that is to be treated with plasma. Such reusable dielectric chambers are sealingly clamped to the workpiece to enclose the surfaces that are to be treated. When the treatment is complete they are unsealed and unclamped.

Because the electrodes are outside of and separate from the chamber, they can be replaced with ease at little cost, thus permitting the electrodes to be optimally shaped for a particular part. The need to only reduce the pressure to from approximately 100 to 1 or 0.1 Torr, rather than down into the millitorr range greatly reduces the equipment and operation costs. Cycle time (the time from the beginning of a cycle through the completion of that cycle to the beginning of the next cycle) is also greatly reduced. Cycle times of less than 10 seconds for the plasma treatment are practical.

The invention is particularly applicable to the special case where the objective is to treat the inside walls of the vacuum chamber itself. Any shape can be treated, but the invention is particularly applicable to hollow dielectric tubes with a length to internal diameter ratio (aspect ratio) of at least 10 to 1, and generally at least 100 to one, or even 1000 to 1 or more. Such a high aspect ratio tube is selected and purged, if desired. One end of the tube is sealed. A vacuum pump is connected to the other end of the tube. The tube is evacuated, for example, to a pressure of approximately 50 to 1 Torr. One or more electrodes are positioned adjacent to but outside of the tube. An oscillating high voltage source is applied to the electrodes. A plasma is caused to form in the evacuated tube by applying such a voltage across the electrodes. The tube and electrodes are moved relative to one another at a rate that permits the surface of the interior wall of the tube (and anything else inside of the tube) to be exposed to the plasma long enough to provide the desired change to the exposed surfaces inside the tube. Generally, when the desired length of tubing has been treated, the vacuum is released, often through a filter. Large reels of tubing with very small inside diameters (for example, 5 millimeters or less) can be treated quickly by passing the evacuated tubing from one real to another between a pair of electrodes. The glow discharge inside of the tube typically extends for several inches on either side of the electrodes.

The present invention also enables the selective treatment of less than all of the surface area of a workpiece. For example, just the edge of a vehicle windshield may be treated to improve the sealing characteristics of the edge. A part of a workpiece may be treated, for example, by placing the workpiece in a treatment chamber, evacuating the chamber to a rough vacuum, positioning plasma generating electrodes in the vicinity of the area of the workpiece that is to be treated, and applying a minimum power so that the resulted plasma just covers approximately the selected area of the workpiece. That is, the plasma zone is smaller than the workpiece.

If the entire surface of a relatively large workpiece needs to be treated with plasma, this may be accomplished according to the present invention without the cost of constructing or operating a system that is large enough to treat the entire workpiece at one time. The entire surface of the workpiece is treated one area at a time by moving the electrodes and the workpiece relative to one another so that the electrodes are scanned over the surface. The plasma zone may be moved continuously or stepwise, as may be desired, to treat as much or as little of the surface of the workpiece as may be required. This incremental scanning allows treating the inside or outside or both surfaces of relatively large workpieces with a minimum amount of power. This is particularly applicable where because of shape, size or other factors it is impossible or impractical to treat an entire workpiece at once. Such incremental scanning operations are also applicable to the plasma treatment of workpieces that are individually encased in separate treatment chambers. The plasma treatment of the inside of an elongated tube is a special case of an incremental scanning operation. The plasma zone may extend for a foot or more within the tube on either side of the electrodes, but it does not extend for the entire length of, for example, a 100 meter long tube. Moving the tube and the electrodes relative to one another allows the entire length of the tube to pass through the plasma treatment zone one increment at a time. Typically, the tube is moved continuously past stationary electrodes at a rate sufficient to provide the desired treatment to the inside wall of the tube. The tube may, however, be moved in separate steps if desired.

In general, the only structural requirement for a dielectric chamber is that it should not collapse when the required vacuum is applied. The shape and size of the chamber should be taken into consideration when designing the chamber since the forces applied to the walls are proportional to surface area and resistance of the material to the outside pressure depends on the distribution of these forces. As a rule, any flat surface structure is more vulnerable to collapse than a curved one. For most plastic materials (thermosetting and thermoplastic) a wall thickness of approximately 2 millimeters for a chamber internal diameter of up to approximately 10 centimeters is generally satisfactory.

For chambers with large surface areas some structural design features may need to be provided to prevent it from collapsing. Some structural brackets or increased wall thickness may be required. In some cases the chamber may have a different shape comparing to the treated article (e.g., a cube inside of a sphere). In general the chamber should follow the contours of the article to minimize the gap between the two. This will generally increase the production rate by allowing the vacuum to be created faster and save power by reducing the high voltage applied to the electrode, and the like.

The desirable gap tolerances for most efficient operations generally range from approximately 0.1 to 1 inch, although they may be larger or smaller depending on the specific application. This wide tolerance in the gap between the surface of the workpiece and the dielectric chamber wall permits the construction of a chamber that is much simpler in shape than the workpiece, and, therefore, easier to make. Gaps of as much as 2 inches or more may be employed, but the volume of the atmosphere that must be adjusted as to pressure, composition, or both is such that the efficiency of the operation generally suffers a significant decline. In general, the efficiency of the operation decreases as the gap increases. The efficiency in terms of capital investment and operation according to the present invention is significant to the importance of the present invention. The voltage and electrode configuration should be such that a breakdown voltage condition occurs inside but not outside of the dielectric chamber. Gaps of approximately 1 inch or less usually minimize the required voltage. The same considerations apply to the gap between the electrodes and the dielectric chamber.

The dielectric strengths of most plastics range from approximately 12,000 to 28,000 Volts per millimeter. Most dielectrics have enough strength to withstand the maximum electrical field created between two opposite electrodes at the applied frequency. For example, a 2 millimeter thick sheet of high-density polyethylene with a dielectric strength of 20,000 Volts per millimeter can generally be used at up to 40 KV between the electrodes.

Where it is desired to treat the interior but not the exterior of a workpiece, a vacuum pack forming operation may be used to create a film like dielectric barrier adhered to the exterior of the workpiece. This is a very easy, inexpensive, quick, and otherwise efficient way to form a dielectric chamber. A vacuum pack forming operation may also be employed to form an evacuated dielectric chamber over a carcass or frame around a workpiece. The carcass or frame provides the necessary gap between the workpiece and the wall of the dielectric chamber to provide a plasma zone. Also, a vacuum pack forming operation may be employed to form a dielectric chamber over a highly porous packaging material such as foam, bubbles, or the like. The highly porous packing material provides the plasma zone in which the plasma forms.

Modifications, combinations, and changes may be made in the embodiments which have been described without departing from the spirit and scope of the accompanying claims. It is therefore to be understood that, within the scope of the appended claims, the invention may be practiced otherwise than as specifically described.

What is claimed is:

1. A method of treating solid exterior surfaces of a plurality of workpieces with a substantially uniform non-thermal dielectric barrier discharge plasma comprising:

selecting a plurality separate dielectric chambers, each said dielectric chamber having a total volume, and a wall, said wall comprising dielectric material, each said dielectric chamber being adapted to confining therein an atmosphere with a near ambient atmospheric pressure and a non-air composition, each said dielectric chamber comprising a handling and storage container for at least a first of said workpieces;

placing said first workpiece in a first of said dielectric chambers, placing a second of said workpieces in a second dielectric chambers, there being a void volume within each of said first and second dielectric chambers between said first and second workpieces and the respective walls of said first and second chambers, the respective said void volumes being less than approximately 30 percent, or approximately 20 percent, or approximately 10 percent of the respective said total volumes;

providing an atmosphere control system, and using said atmosphere control system to flush said first and second dielectric chambers and adjust said non-air compositions to predetermined values, and sealing said first and second dielectric chambers said predetermined values being adapted to allowing the formation of said substantially uniform non-thermal dielectric barrier discharge plasma in a plasma zone in each of said first and second dielectric chambers;

supplying at least one electrode and positioning said one electrode outside of said sealed first dielectric chamber, said dielectric material being generally between said one electrode and said solid exterior surface, and said plasma zone generally being in a gap between said dielectric material and said solid exterior surface, said electrode being operatively connected to a source of plasma generating electrical power;

applying said plasma generating electrical power to said electrode to generate said substantially uniform non-thermal dielectric barrier discharge plasma in said plasma zone;

treating said solid exterior surface with said substantially uniform non-thermal dielectric barrier discharge plasma;

handling and storing said first workpiece with a resulting treated solid exterior surface in said sealed first dielectric chamber;

positioning said one electrode outside of said sealed second dielectric chamber, said dielectric material being generally between said one electrode and said solid exterior surface, and said plasma zone generally being in a gap between said dielectric material said solid exterior, surface, said electrode being operatively connected to a source of plasma generating electrical power;

applying said plasma generating electrical power to said electrode to generate said substantially uniform non-thermal dielectric barrier discharge plasma in said plasma zone;

treating said solid exterior surface with said substantially uniform non-thermal dielectric barrier discharge plasma; and handling and storing said second workpiece with a resulting treated solid exterior surface in said sealed second dielectric chamber.

2. A method of claim 1 wherein said void volume is less than approximately 30 percent of said total volume.

3. A method of claim 1 wherein said gap is less than approximately 1 inch wide.

4. A method of claim 1 wherein said plasma zone is smaller than said first workpiece.

5. A method of claim 1 wherein said placing said first workpiece in said dielectric chamber includes placing at least said solid exterior surface within said first dielectric chamber.

6. A method of claim 1 wherein said solid exterior surface is stationary relative to said plasma zone while being treated with said substantially uniform non-thermal dielectric barrier discharge plasma.

7. A method of claim 1 wherein said first workpiece is a length of hollow tubing, and said solid exterior surface is on the outside of said hollow tubing.

8. A method of claim 1 further comprising providing regulating indicia in association with said first workpiece and regulating at least one of said plasma generating electrical power and said adjusting said non-air composition responsive to information derived from said regulating indicia.

9. A method of claim 1 wherein said solid exterior surface is on the exterior of said solid first workpiece.

10. A method of claim 1 wherein said one electrode is irregular shaped and adapted to generate said substantially uniform non-thermal dielectric barrier discharge plasma to modify the properties of said solid exterior surface in a pattern that is approximately determined by the irregular shape of said one electrode.

11. A method of claim 1 wherein said plasma zone includes a plurality of plasma zones.

12. A method of claim 1 wherein said first workpiece includes a plurality of said solid exterior surfaces, 13. A method of claim 1 wherein said supplying at least one electrode includes supplying at least two electrodes positioned outside of said sealed first dielectric chamber.

14. A method of claim 1 including establishing relative motion between said solid exterior surface and said one electrode.

15. A method of claim 1 further comprising placing a plurality of said. solid exterior surfaces in said first dielectric chamber.

* * * * *